US009957305B2

(12) United States Patent
Ballard et al.

(10) Patent No.: US 9,957,305 B2
(45) Date of Patent: May 1, 2018

(54) ANTI-C. DIFFICILE TOXIN ANTIBODIES AND ASSOCIATED METHODS

(75) Inventors: Jimmy D. Ballard, Norman, OK (US); Jordi M. Melton, Norman, OK (US); Latisha Heinlen, Oklahoma City, OK (US); Elaine E. Hamm, Oklahoma City, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 546 days.

(21) Appl. No.: 14/344,749

(22) PCT Filed: Sep. 13, 2012

(86) PCT No.: PCT/US2012/055228

§ 371 (c)(1), (2), (4) Date: Dec. 29, 2014

(87) PCT Pub. No.: WO2013/040254
PCT Pub. Date: Mar. 21, 2013

(65) Prior Publication Data

US 2015/0104454 A1 Apr. 16, 2015

Related U.S. Application Data

(60) Provisional application No. 61/534,298, filed on Sep. 13, 2011.

(51) Int. Cl.

| | |
|---|---|
| *A61K 38/00* | (2006.01) |
| *C07K 14/33* | (2006.01) |
| *A61K 39/08* | (2006.01) |
| *C07K 16/12* | (2006.01) |
| *G01N 33/569* | (2006.01) |

(52) U.S. Cl.

CPC .............. *C07K 14/33* (2013.01); *A61K 39/08* (2013.01); *C07K 16/1282* (2013.01); *G01N 33/56911* (2013.01); *G01N 2333/33* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 2003/0054493 | A1 | 3/2003 | Williams et al. |
| 2009/0087478 | A1 | 4/2009 | Hansen et al. |

*Primary Examiner* — Ja'Na Hines
*Assistant Examiner* — Khatol Shahnan Shah
(74) *Attorney, Agent, or Firm* — Winstead PC

(57) ABSTRACT

Embodiments of the invention are directed to a composition comprising a recombinant protein in soluble form wherein said recombinant protein comprises a portion of the *Clostridium difficile* toxin B sequence that comprises an epitope for anti-toxin B antibody. Other embodiments of the invention are directed to the generation of antibodies using peptide fragments of *C. difficile* toxin B.

1 Claim, 3 Drawing Sheets

FIG. 2

ANTI-C. DIFFICILE TOXIN ANTIBODIES AND ASSOCIATED METHODS

CROSS-REFERENCES TO RELATED APPLICATIONS

This Application claims the benefit under 35 U.S.C. 119(e) of U.S. Provisional Patent Application Ser. No. 61/534,298 filed Sep. 13, 2011, which is incorporated herein by reference in its entirety as if fully set forth herein.

STATEMENT REGARDING FEDERALLY-SPONSORED RESEARCH OR DEVELOPMENT

This invention was made with government support under Grant No. R01HL084489 awarded by the National Institutes of Health. The government has certain rights in the invention.

BACKGROUND OF THE INVENTION

*Clostridium difficile* is a Gram positive, spore forming anaerobic *bacillus*, and many strains of this species have acquired resistance to a majority of commonly used antibiotics. The reduction of microflora as an effect of use of antibiotics allows *C. difficile* to grow and to produce harmful toxins in the intestine, without nutritional competition from normal bacterial flora. Highly virulent strains of *C. difficile* result in increased incidence of illness and more severe effects in patients.

*C. difficile* produces two major protein toxins, toxin A (TcdA) and toxin B (TcdB), which are 308 kD and 269 kD respectively in size. The two toxins belong to the large clostridial cytotoxin (LCT) family and share 49% amino acid identity. The toxins have similar structures and share putative receptor binding, transmembrane, and enzymatic domains. After receptor-mediated internalization and intracellular cleavage, the toxins glucosylate members of the Rho-Rac family of small GTPases at a specific threonine residue in host intestinal epithelial cells, leading to alterations in the actin cytoskeleton, massive fluid secretion, acute inflammation, and necrosis of the colonic mucosa.

TcdB has been determined to be the critical virulence factor that contributes to illness, and is a target for diagnosis and vaccination. Neutralizing antibodies against toxin A and toxin B are thought to play an important role in the resolution of *C. difficile*-associated diarrhea (CDAD). Variations in these neutralizing responses, the absence of a neutralizing response, and the lack of cross-neutralization are all hypothesized to contribute to the range of disease severity and the potential relapse. By determining the specific shared and unique neutralizing epitopes, improved diagnostics can be designed (for disease severity, strain type, and relapse potential) as vaccines, and therapeutics for CDAD.

Several studies support the notion that antibodies to toxin A and toxin B protect against CDI. Most patients with acute infection do not exhibit an IgM response, but rather a secondary IgG response. In patients with acute *C. difficile* infection (CDI), higher levels of anti-toxin B IgG have been associated with milder disease. The development of high titers of anti-toxin A antibodies are associated with development of asymptomatic carriage, whereas low titers of anti-toxin A antibodies are associated with the subsequent development of CDI. Low levels of antibodies against toxin A have also been associated with more severe disease. Interestingly, up to 60% of healthy adults have detectable serum IgG and IgA against toxin A and toxin B, but the neutralizing effects of these antibodies wanes in the elderly. Thus, while there are clear correlations between protection against CDI and the presence of neutralizing antibodies, the reasons for loss of these responses with age remain unclear. This is due to the current lack of understanding of what constitutes a strong neutralizing response (i.e. which epitopes matter in a neutralizing response), which makes it difficult to study anti-toxin responses in humans.

Information on neutralizing antibody responses in humans could provide a powerful prognostic tool. It is unclear why some patients will develop severe infection when exposed to a pathogenic strain of *C. difficile*, while others only experience mild-diarrhea. It is very likely that neutralizing antibodies are a critical determinant in disease severity. By further analyzing the immune response present in patients with infection we hope to understand which antibodies are protective of severe or relapsing disease. Preliminary data shows that a majority of patients do indeed make antibodies against toxin B, but many of these "Ab-positive" patients do not produce neutralizing antibodies. Moreover, it has been shown that some patients make antibodies that neutralize toxin B from a hypervirulent strain of *C. difficile* but do not neutralize toxin B from a historical strain of *C. difficile*. In support of this observation, it has also found been found in animal models that antibodies do not cross neutralize the two forms of toxin B. The fact that toxin B antibodies from historical and hypervirulent strains do not cross-neutralize raises several concerns. First, vaccines developed towards the historical toxin may not protect against the hypervirulent toxin. Second, therapeutic monoclonal antibodies may not cross protect. Third, acquired immunity by infection with a historical strain or hypervirulent strain may not protect against infection with the reciprocal strain. For these reasons, there is a critical need to better understand what constitutes a neutralizing anti-toxin response in *C. difficile* infected patients, and to develop a suitable anti-toxin that may be used to protected against CDI and CDAD. Embodiments of the claimed invention set forth herein provides the specific regions of toxin B that are antigenic in humans and animal models and are responsible for neutralization of toxin B. Other embodiments of the invention provide platforms for the expression of large quantities of the toxin B peptide fragments that are used to raise antibodies against toxin B.

SUMMARY OF THE INVENTION

An embodiment of the invention is directed to a composition comprising a recombinant protein in soluble form wherein said recombinant protein comprises a portion of the *Clostridium difficile* toxin B sequence that is used to produce an antibody that neutralizes toxin B.

A further embodiment of the invention is directed to an isolated polypeptide, the amino acid sequence of which comprises a sequence containing a fragment of *Clostridium difficile* toxin B sequence, wherein the fragment is an antigen for producing anti-toxin B antibodies.

BRIEF DESCRIPTION OF THE DRAWINGS

FIG. 2 shows the results of a test of antibodies against various *C. difficile* fragments for toxin-neutralizing ability.

DETAILED DESCRIPTION OF EXEMPLARY EMBODIMENTS

*C. difficile* is a gram-positive, spore forming, anaerobic bacterium. It is the leading cause of antibiotic-associated diarrhea, the severity of which ranges from mild diarrhea to life threatening pseudomembranous colitis. Pathogenic *C. difficile* strains excrete exotoxins A (TcdA) and B (TcdB) that have been intimately linked to its pathogenicity. Both TcdA and TcdB are enterotoxic, capable of inducing intestinal epithelial damage and increasing mucosal permeability, and hence are thought to be responsible for the pathogenesis of *C. difficile*-associated colitis. Several hospital outbreaks of CDAD, with high morbidity and mortality in the past few years in North America, have been attributed to the widespread use of broad-spectrum antibiotics. The emergence of more virulent *C. difficile* strains is also contributing to the increased incidence and severity of the disease. Antibiotic usage results in a reduction of commensal microflora in the gut, which permits *C. difficile* to proliferate more extensively, leading to the production of toxins. CDAD has a range of symptoms varying from mild diarrhea to severe fulminate lethal disease.

Embodiments of the invention provided herein include a vector for recombinant high level expression of a *C. difficile* peptide fragment. In various embodiments the vector is a shuttle vector. Further provided herein is a cell that carries the vector expressing a *C. difficile* peptide fragment. The invention herein also features a kit for assay for the presence of *C. difficile* such that the kit includes at least one peptide fragment. The kit in certain embodiments includes instructions for use. In other embodiments the kit includes at least one toxin neutralizing antibody.

Antibodies against toxin A and toxin B have been identified in patients with previous or current infection with *C. difficile*. Patient and control sera samples were collected, stored, and tested for reactivity against purified toxins A and B (from both 10463 and NAP1 strains) using standard ELISA assays. Toxin was purified primarily from two strains: 10463 and NAP1.

An embodiment of the invention is directed to a toxin neutralization assay. In this assay, sera from patients was tested for the ability to neutralize Toxin B. Toxin B from *C. difficile* was incubated with sera from patients infected with *C. difficile* for 1 hour at room temperature. The sera/toxin mixture was added to Chinese Hamster Ovary (CHO) cells and incubated at 37° C. The CHO cells were viewed under the microscope for cell viability. It was observed that CHO cells that were treated with the sera/toxin mixture exhibited greater viability than cells treated with toxin alone.

Figure 1:
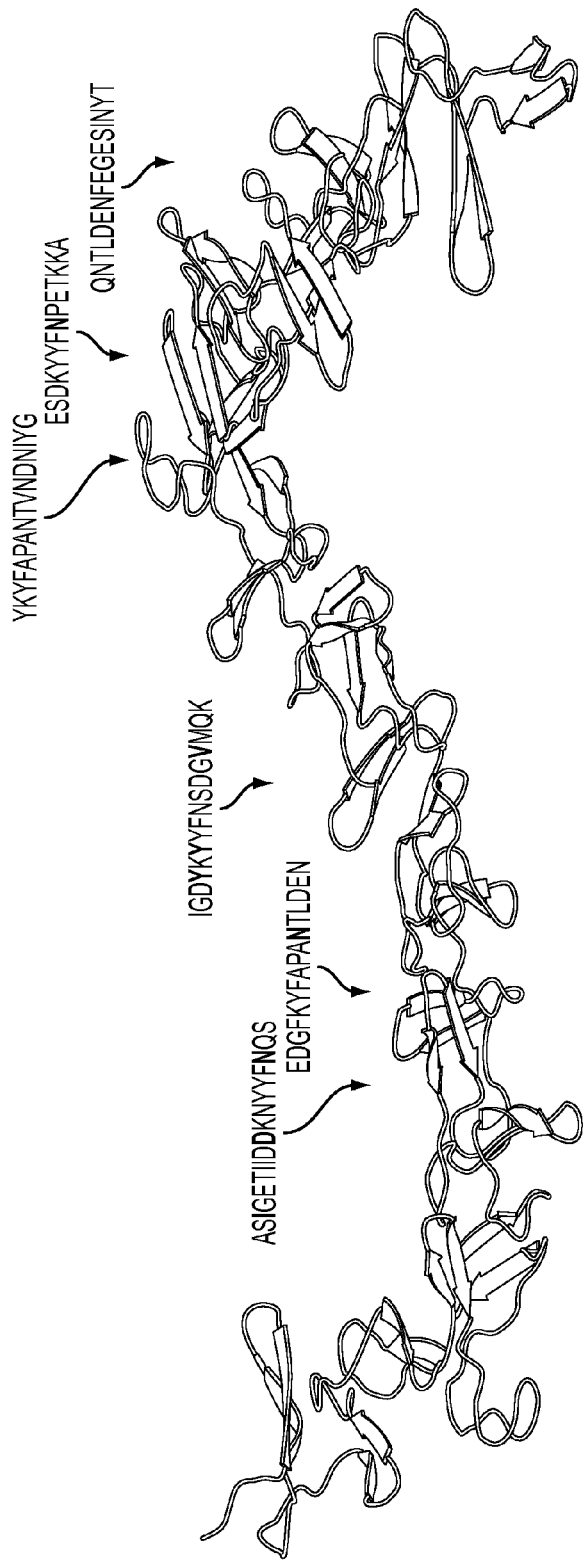
FIG. 1 shows regions of the Toxin B protein that are recognized by anti-Toxin B antibody.

An embodiment of the invention is directed to determining regions of the Toxin B protein that are recognized by anti-Toxin B antibody (FIG. 1). Experiments were carried out in order to determine epitope recognition by anti-Toxin B antibody, using antisera from patients infected with *C. difficile*. Several regions of the Toxin B protein were identified as regions targeted by the anti-toxin B antibody. These regions are identified below and in the accompanying sequence listings:

```
                                         (SEQ ID NO: 1)
ASIGETIIDDKNYYFNQS-1874 to 1891

(SEQ ID NO: 2)
EDGFKYFAPANTLDEN-1902 to 1917

(SEQ ID NO: 3)
IGDYKYFNSDGVMQK-1972 to 1987

(SEQ ID NO: 4)
YKYFAPANTVNDNIYG-2168 to 2183

(SEQ ID NO: 5)
ESDKYYFNPETKKA-2218 to 2231

(SEQ ID NO: 6)
QNTLDENFEGESINYT-2308 to 2323
```

Figure 2:
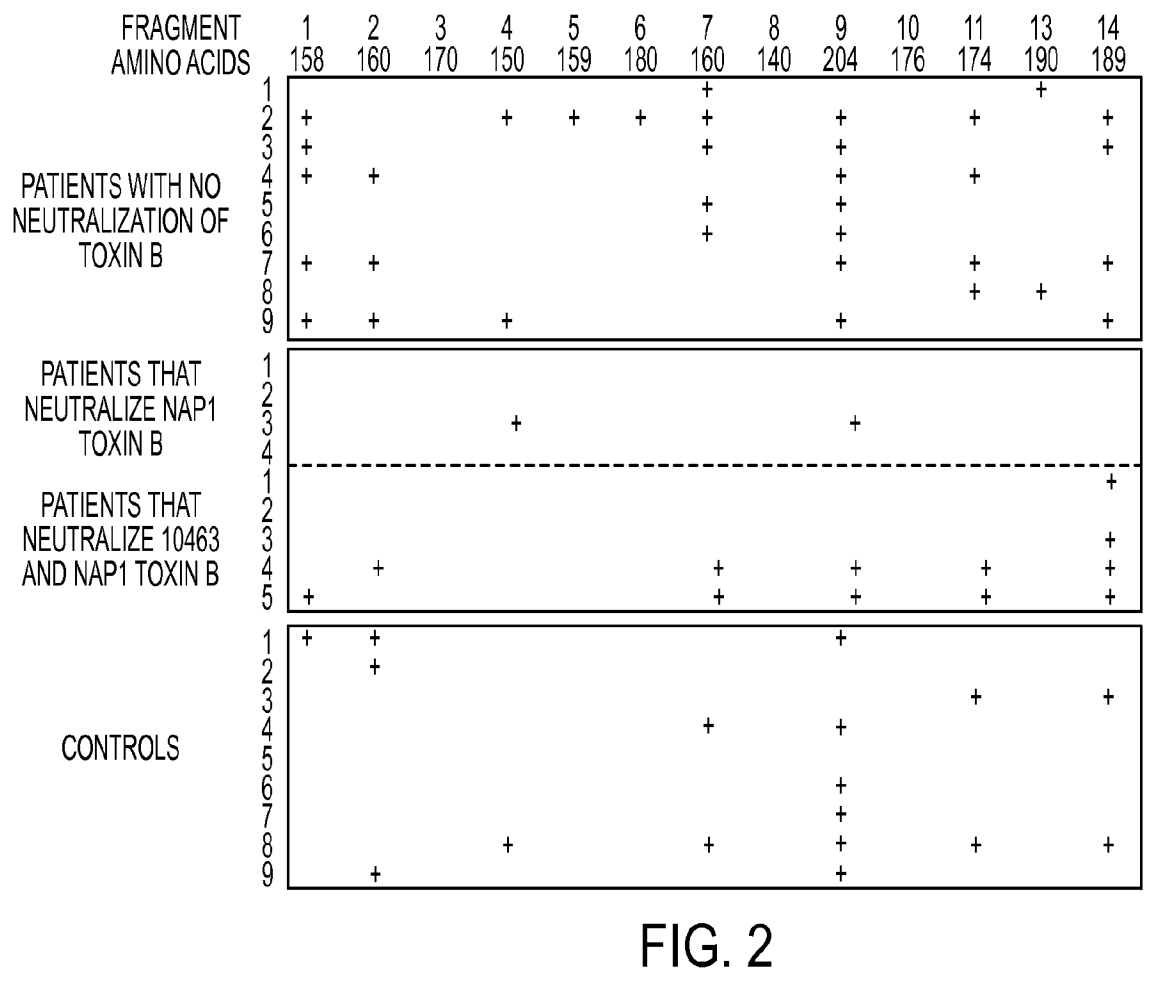

An embodiment of the invention is directed to determining regions of the toxin B protein that are targeted during neutralization of toxin B. Serum samples with neutralizing antibodies were analyzed using multiple fragments of toxin to detect which region of the toxin B protein was targeted among patients exhibiting neutralizing antibody responses. The fragments were cloned and expressed. As shown in FIG. 2, antibodies against a peptide fragment (fragment 14) of the 10463 strain toxin B were associated with neutralization in vitro. This fragment is a 189 amino acid polypeptide and spans amino acids 2152 to 2341 of toxin B from the 10463 strain. This sequence is set forth below and as SEQ ID NO: 7 in this application.

```
                                         (SEQ ID NO: 7)
DDNGIVQIGVEDTSDGYKYFAPANTVNDNIYGQAVEYSGLVRVGEDV

YYFGETYTIETGWIYDMENESDKYYFNPETKKACKGINLIDDIKYYF

DEKGIMRTGLISFENNNYYFNENGEMQFGYINIEDKMFYFGEDGVMQ

IGVENTPDGEKYFAHQNTLDENFEGESINYTGWLDLDEKRYYFTDEY

IA
```

In another embodiment of the invention, antibodies generated against a peptide fragment derived from NAP1 toxin B was tested for neutralization of toxin B in vitro. This fragment spans amino acids 2152 to 2341 of toxin B from the NAP1 strain. This sequence is set forth below and as SEQ ID NO: 8 in this application.

```
                                         (SEQ ID NO: 8)
DENGLVQIGVFDTSDGYKYFAPANTVNDNIYGQAVEYSGLVRVGEDV

YYFGETYTIETGWIYDMENESDKYYFDPETKKAYKGINVIDDIKYYF

DENGIMRTGLITFEDNHYYFNEDGIMQYGYLNIEDKTFYFSEDGIMQ

IGVFNTPDGFKYFAHQNTLDENFEGESINYTGWLDLDEKRYYFTDEY

IA
```

An embodiment of the invention is directed to determining antigenic portions of the Toxin B protein. Overlapping decapeptides were synthesized for the fragments of interest and patient antibody responses were finely dissected to determine exactly which sequences are antigenic and associated with neutralization.

Figure 3:
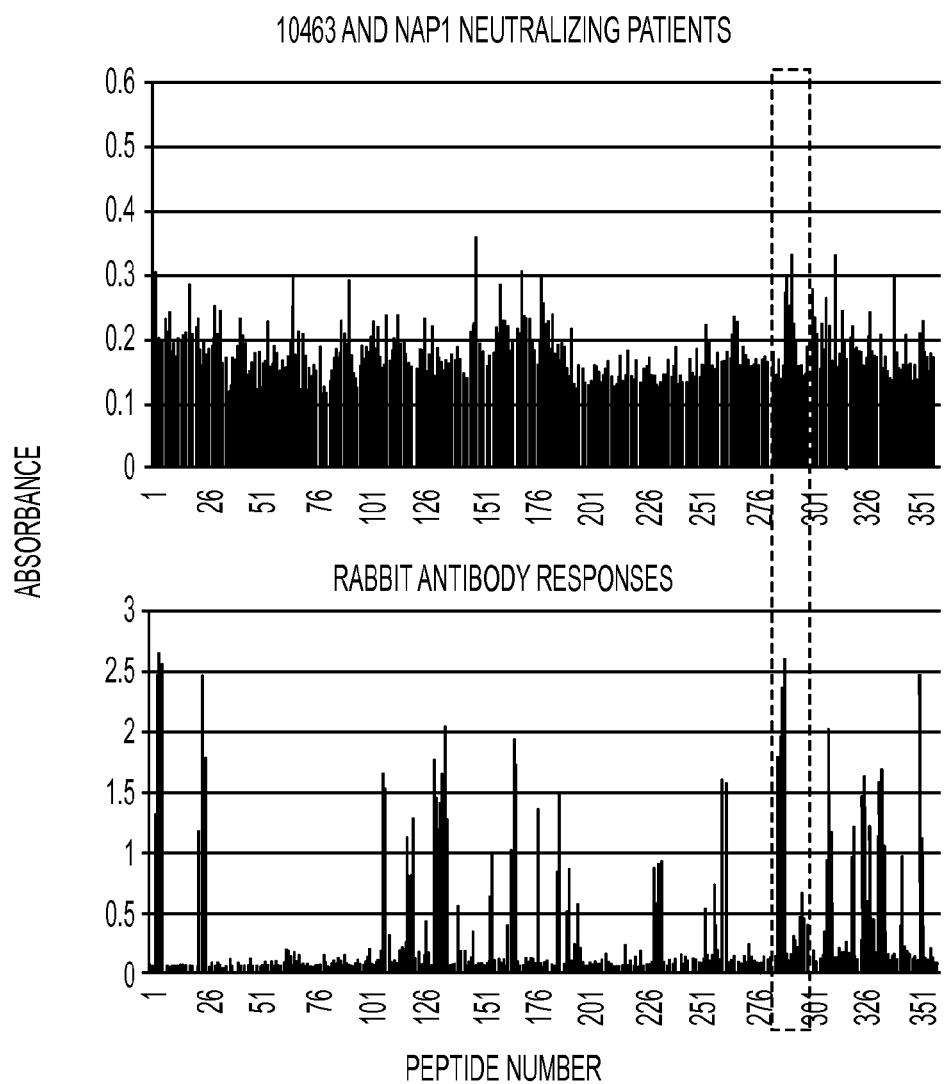
FIG. 3 shows the results of epitope mapping to identify neutralizing antibody-producing peptide fragments.

Fine specificity epitope mapping using overlapping decapapetides narrowed the region of interest down to one region that is targeted in both the animal model as well as patient samples, and antibodies to which are capable of neutralizing 10463 and NAP1 toxin in vitro (FIG. 3). As is shown in FIG.

3, the dashed box represents the boundaries of the region in the toxin B proteins that appear to be targeted by anti-toxin B antibodies in experiments and also demonstrate toxon B neutralizing properties. The identified peptide has the following amino acid sequence: ESDKYYFNPETKKACK-GINLID (SEQ ID NO:9). This sequence overlaps with SEQ ID NO:5 that was previously identified as a region of toxin B that is targeted by anti-toxin B antibodies.

A further analysis of the two toxin B fragments derived from the 10463 (SEQ ID NO:7) and NAP1 (SEQ ID NO:8) strains shows that the fragments share a hexapeptide namely PETKKA (SEQ ID NO:10), which represents the peptide at positions 2226 to 2231.

An embodiment of the invention is directed to a composition comprising an antigenic peptide fragment derived from *C. difficile* toxin B. In certain embodiments of the invention, the antigenic peptide fragments are included in expression vectors, which in turn are used to produce quantities of protein that can be used to raise antibodies.

An embodiment of the invention is directed to raising antibodies that target epitopes in the Toxin B protein. Other embodiments of the invention are directed to raising antibodies that target epitopes in the toxin B protein and exhibit a neutralizing effect. Rabbits were immunized with a fragment of toxin B and sera were collected at multiple timepoints. Rabbit sera were tested for the presence of antibodies as well as neutralizing potential of the antibodies.

An embodiment of the invention provides a method for diagnosing *C. difficile* infection comprising the steps of (a) contacting a biological sample of a subject with at least one peptide fragment, wherein said at least one peptide fragment is a fragment of toxin B; and (b) detecting antigen-antibody complex formation. In this method, the biological sample of the subject may contain antibodies that can complex with the peptide fragments used in testing. An example of such a biological sample is the sera of a test subject.

Another embodiment of the invention provides a kit comprising one or more peptide fragments of Toxin B, wherein the kit is used to test sera from patients with previous or current infection with *C. difficile*. The results of the test obtained using the kit provides a diagnosis of the type of infection that has a patient has had, i.e., the strain of *C. difficile* that caused the infection. An alternate use of the kit is to serve as a therapeutic aid in the prevention and treatment of *C. difficile* infection. For example, peptide fragments of Toxin B may be used to immunize patients such that antibodies resulting from the immunization would serve to neutralize the toxin response in the event of a subsequent infection by *C. difficile*.

A skilled person will recognize that many suitable variations of the methods may be substituted for or used in addition to those described above and in the claims. It should be understood that the implementation of other variations and modifications of the embodiments of the invention and its various aspects will be apparent to one skilled in the art, and that the invention is not limited by the specific embodiments described herein and in the claims. Therefore, it is contemplated to cover the present embodiments of the invention and any and all modifications, variations, or equivalents that fall within the true spirit and scope of the basic underlying principles disclosed and claimed herein.

What is claimed is:

1. A method of generating a neutralizing antitoxin directed against *Clostridium difficile* toxin B comprising: a) providing: i) a purified recombinant protein comprising a portion of the *Clostridium difficile* toxin B protein, wherein the portion of toxin B protein is selected from the group consisting of SEQ ID NO: 3, and wherein said recombinant protein is expressed in soluble form, and ii) a host; and b) immunizing said host with said recombinant protein in an amount sufficient to generate an antitoxin effective in neutralizing *Clostridium difficile* toxin B in vivo.

* * * * *

SEQUENCE LISTING

```
<160> NUMBER OF SEQ ID NOS: 10

<210> SEQ ID NO 1
<211> LENGTH: 18
<212> TYPE: PRT
<213> ORGANISM: Clostridium difficile
<220> FEATURE:
<221> NAME/KEY: PEPTIDE
<222> LOCATION: (1)..(18)

<400> SEQUENCE: 1

Ala Ser Ile Gly Glu Thr Ile Ile Asp Asp Lys Asn Tyr Tyr Phe Asn
1               5                   10                  15

Gln Ser

<210> SEQ ID NO 2
<211> LENGTH: 16
<212> TYPE: PRT
<213> ORGANISM: Clostridium difficile
<220> FEATURE:
<221> NAME/KEY: PEPTIDE
<222> LOCATION: (1)..(16)

<400> SEQUENCE: 2

Glu Asp Gly Phe Lys Tyr Phe Ala Pro Ala Asn Thr Leu Asp Glu Asn
1               5                   10                  15

<210> SEQ ID NO 3
<211> LENGTH: 15
<212> TYPE: PRT
<213> ORGANISM: Clostridium difficile
<220> FEATURE:
<221> NAME/KEY: PEPTIDE
<222> LOCATION: (1)..(15)
```

```
<400> SEQUENCE: 3

Ile Gly Asp Tyr Lys Tyr Phe Asn Ser Asp Gly Val Met Gln Lys
1               5                   10                  15

<210> SEQ ID NO 4
<211> LENGTH: 16
<212> TYPE: PRT
<213> ORGANISM: Clostridium difficile
<220> FEATURE:
<221> NAME/KEY: PEPTIDE
<222> LOCATION: (1)..(16)

<400> SEQUENCE: 4

Tyr Lys Tyr Phe Ala Pro Ala Asn Thr Val Asn Asp Asn Ile Tyr Gly
1               5                   10                  15

<210> SEQ ID NO 5
<211> LENGTH: 14
<212> TYPE: PRT
<213> ORGANISM: Clostridium difficile
<220> FEATURE:
<221> NAME/KEY: PEPTIDE
<222> LOCATION: (1)..(14)

<400> SEQUENCE: 5

Glu Ser Asp Lys Tyr Tyr Phe Asn Pro Glu Thr Lys Lys Ala
1               5                   10

<210> SEQ ID NO 6
<211> LENGTH: 16
<212> TYPE: PRT
<213> ORGANISM: Clostridium difficile
<220> FEATURE:
<221> NAME/KEY: PEPTIDE
<222> LOCATION: (1)..(16)

<400> SEQUENCE: 6

Gln Asn Thr Leu Asp Glu Asn Phe Glu Gly Gly Ser Ile Asn Tyr Thr
1               5                   10                  15

<210> SEQ ID NO 7
<211> LENGTH: 190
<212> TYPE: PRT
<213> ORGANISM: Clostridium difficile
<220> FEATURE:
<221> NAME/KEY: PEPTIDE
<222> LOCATION: (1)..(190)

<400> SEQUENCE: 7

Asp Asp Asn Gly Ile Val Gln Ile Gly Val Phe Asp Thr Ser Asp Gly
1               5                   10                  15

Tyr Lys Tyr Phe Ala Pro Ala Asn Thr Val Asn Asp Asn Ile Tyr Gly
                20                  25                  30

Gln Ala Val Glu Tyr Ser Gly Leu Val Arg Val Gly Glu Asp Val Tyr
            35                  40                  45

Tyr Phe Gly Glu Thr Tyr Thr Ile Glu Thr Gly Trp Ile Tyr Asp Met
        50                  55                  60

Glu Asn Glu Ser Asp Lys Tyr Tyr Phe Asn Pro Glu Thr Lys Lys Ala
65                  70                  75                  80

Cys Lys Gly Ile Asn Leu Ile Asp Asp Ile Lys Tyr Tyr Phe Asp Glu
                85                  90                  95

Lys Gly Ile Met Arg Thr Gly Leu Ile Ser Phe Glu Asn Asn Asn Tyr
            100                 105                 110
```

```
Tyr Phe Asn Glu Asn Gly Glu Met Gln Phe Gly Tyr Ile Asn Ile Glu
            115                 120                 125

Asp Lys Met Phe Tyr Phe Gly Glu Asp Gly Val Met Gln Ile Gly Val
        130                 135                 140

Phe Asn Thr Pro Asp Gly Phe Lys Tyr Phe Ala His Gln Asn Thr Leu
145                 150                 155                 160

Asp Glu Asn Phe Glu Gly Glu Ser Ile Asn Tyr Thr Gly Trp Leu Asp
            165                 170                 175

Leu Asp Glu Lys Arg Tyr Tyr Phe Thr Asp Glu Tyr Ile Ala
            180                 185                 190

<210> SEQ ID NO 8
<211> LENGTH: 190
<212> TYPE: PRT
<213> ORGANISM: Clostridium difficile
<220> FEATURE:
<221> NAME/KEY: PEPTIDE
<222> LOCATION: (1)..(190)

<400> SEQUENCE: 8

Asp Glu Asn Gly Leu Val Gln Ile Gly Val Phe Asp Thr Ser Asp Gly
1               5                   10                  15

Tyr Lys Tyr Phe Ala Pro Ala Asn Thr Val Asn Asp Asn Ile Tyr Gly
            20                  25                  30

Gln Ala Val Glu Tyr Ser Gly Leu Val Arg Val Gly Glu Asp Val Tyr
        35                  40                  45

Tyr Phe Gly Glu Thr Tyr Thr Ile Glu Thr Gly Trp Ile Tyr Asp Met
    50                  55                  60

Glu Asn Glu Ser Asp Lys Tyr Tyr Phe Asp Pro Glu Thr Lys Lys Ala
65                  70                  75                  80

Tyr Lys Gly Ile Asn Val Ile Asp Asp Ile Lys Tyr Tyr Phe Asp Glu
            85                  90                  95

Asn Gly Ile Met Arg Thr Gly Leu Ile Thr Phe Glu Asp Asn His Tyr
            100                 105                 110

Tyr Phe Asn Glu Asp Gly Ile Met Gln Tyr Gly Tyr Leu Asn Ile Glu
            115                 120                 125

Asp Lys Thr Phe Tyr Phe Ser Glu Asp Gly Ile Met Gln Ile Gly Val
        130                 135                 140

Phe Asn Thr Pro Asp Gly Phe Lys Tyr Phe Ala His Gln Asn Thr Leu
145                 150                 155                 160

Asp Glu Asn Phe Glu Gly Glu Ser Ile Asn Tyr Thr Gly Trp Leu Asp
            165                 170                 175

Leu Asp Glu Lys Arg Tyr Tyr Phe Thr Asp Glu Tyr Ile Ala
            180                 185                 190

<210> SEQ ID NO 9
<211> LENGTH: 22
<212> TYPE: PRT
<213> ORGANISM: Clostridium difficile
<220> FEATURE:
<221> NAME/KEY: PEPTIDE
<222> LOCATION: (1)..(22)

<400> SEQUENCE: 9

Glu Ser Asp Lys Tyr Tyr Phe Asn Pro Glu Thr Lys Lys Ala Cys Lys
1               5                   10                  15

Gly Ile Asn Leu Ile Asp
            20
```

```
<210> SEQ ID NO 10
<211> LENGTH: 6
<212> TYPE: PRT
<213> ORGANISM: Clostridium difficile
<220> FEATURE:
<221> NAME/KEY: PEPTIDE
<222> LOCATION: (1)..(6)

<400> SEQUENCE: 10

Pro Glu Thr Lys Lys Ala
1               5
```